United States Patent [19]

Ikeda et al.

[11] Patent Number: 4,688,058

[45] Date of Patent: Aug. 18, 1987

[54] THERMAL RECORDING MATERIALS

[75] Inventors: Haruhiko Ikeda; Shigetoshi Hiraishi, both of Tokyo, Japan

[73] Assignee: Mitsubishi Paper Mills, Ltd., Tokyo, Japan

[21] Appl. No.: 932,346

[22] Filed: Nov. 19, 1986

[30] Foreign Application Priority Data

Nov. 20, 1985 [JP] Japan ................................ 60-262006
Dec. 25, 1985 [JP] Japan ................................ 60-295861
Dec. 25, 1985 [JP] Japan ................................ 60-295862
Dec. 25, 1985 [JP] Japan ................................ 60-295863
Dec. 25, 1985 [JP] Japan ................................ 60-295864
Dec. 26, 1985 [JP] Japan ................................ 60-295602
Dec. 28, 1985 [JP] Japan ................................ 60-297935

[51] Int. Cl.$^4$ ............................................ B41M 5/18
[52] U.S. Cl. .................................. 503/209; 503/208; 503/216; 427/150
[58] Field of Search ............... 346/208, 209, 216, 225; 427/150-152

[56] References Cited

U.S. PATENT DOCUMENTS 4,480,052 10/1984 Ichijima et al. ................ 346/209
4,644,375 2/1987 Satake et al. .................... 346/208

FOREIGN PATENT DOCUMENTS 0064594 4/1982 Japan ............................ 346/209
0122193 6/1985 Japan ............................ 346/209

Primary Examiner—Bruce H. Hess
Attorney, Agent, or Firm—Cushman, Darby & Cushman

[57] ABSTRACT

A highly sensitive thermal recording material excellent in response to heat is obtained by incorporating as a sensitizer at least one compound into a thermal printing material comprising a usually colorless or light-colored dye precursor and a developer which reacts with each other to develop color on heating, said compound being selected from the following compounds represented by the following general formulas (I), (II) and (III):

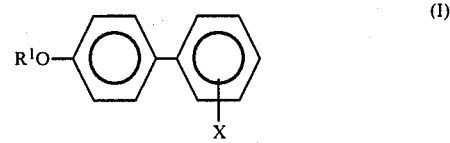

(I)

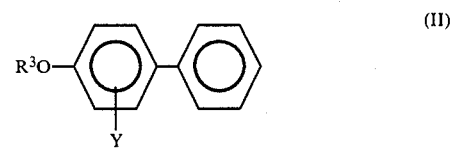

(II)

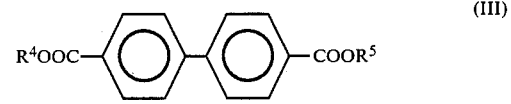

(III)

26 Claims, No Drawings

THERMAL RECORDING MATERIALS

BACKGROUND OF THE INVENTION

This invention relates to a highly sensitive thermal recording material excellent in response to heat.

Thermal recording materials are generally composed of a support and a thermal recording layer formed thereon composed mainly of a usually colorless or light-colored electron-donative dye precursor and an electron-accepting developer. When they are heated by a thermal head, thermal pin, laser or the like, the dye precursor reacts with the developer in a moment to give recorded images. They are disclosed in Japanese Patent Publication Nos. 4160/68 and 14039/70, etc. Such thermal recording materials are advantageous in that a record can be obtained by means of a relatively simple apparatus, that their maintenance is easy, and that they cause no noise. They are utilized in various fields of recorders for measurement, facsimile, printers, terminals of computer, label, automatic ticket machines for passanger tickets and the like, etc. Particularly in facsimile, there is a greatly growing demand for thermal recording. Moreover, facsimile is being made high-speed for the purpose of reducing transmission cost. With such speedup of facsimile, the thermal recording materials have come to be required to have higher sensitivity.

In high-speed facsimile, a standard manuscript of the A4 size is transmitted and received in several to 20 seconds, and therefore a current flows to a facsimile thermal head repeatedly for a very short time of several milliseconds or less every time, and heat energy produced thereby is transmitted to a thermal recording sheet to carry out an image formation reaction.

In order to carry out the image formation reaction by means of heat energy in such a short time, it is necessary to use a thermal recording material excellent in response to heat. For increasing its heat-reactivity, its compatibility between the developer and the dye precursor should be improved. For this purpose, a sensitizer is used if necessary. Since the sensitizer dissolve or enclose the neighboring dye precursor and developer to promote a color reaction when melted by the transmitted heat energy, improvement of the response to heat of the developer or its compatibility with the dye precursor and the developer is one method for making the thermal recording material highly sensitive.

As such a method, there are disclosed the addition of waxes in Japanese Patent Application Kokai (Laid-Open) No. 19231/73; that of nitrogen-containing compounds, carboxylic acid esters, etc. in Japanese Patent Application Kokai (Laid-Open) Nos. 34842/74, 149353/75, 106746/77, 5636/78, etc.; that of naphthol derivatives in Japanese Patent Application Kokai (Laid-Open ) Nos. 64593/82 and 87094/83; that of naphthoic acid derivatives in Japanese Patent Application Kokai (Laid-Open) 64592/82, 185187/82, 191089/82 and 110289/83; that of benzoic acid ester derivatives in Japanese Patent Application (Kokai) Nos. 148688/82, 182483/82, 112788/83 and 162379/83.

However, thermal recording materials produced by employing these methods are still insufficient in depth of developed color and sensibility of color development.

The present inventors have investigated various sensitizers in order to obtain a highly sensitive thermal recording material more excellent in response to heat.

SUMMARY OF THE INVENTION

A highly sensitive thermal recording material excellent in response to heat could be obtained by incorporating as a sensitizer at least one compound into a thermal recording material comprising a usually colorless or light-colored dye precursor and a developer which reacts therewith to cause color development thereof on heating, said compound being selected from the group consisting of compounds represented by the general formulas (I), (II) and (III):

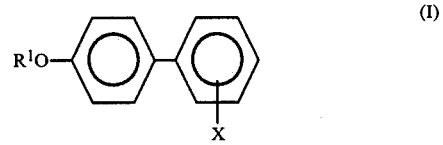

(I)

wherein $R^1$ is a substituted or unsubstituted alkenyl group, a substituted or unsubstituted cycloalkyl group, a substituted or unsubstituted cycloalkylcarbonyl group, a substituted or unsubstituted alkynyl group, or a substituted or unsubstituted alkenylcarbonyl group, and X is a hydrogen atom, an alkoxy group, an aralkyloxy group, an aroyloxy group, an alkenyloxy group or $R^2O-$ in which $R^2$ is a substituted or unsubstituted cycloalkyl group, a substituted or unsubstituted cycloalkylcarbonyl group, a substituted or unsubstituted alkynyl group, or a substituted or unsubstituted alkenylcarbonyl group;

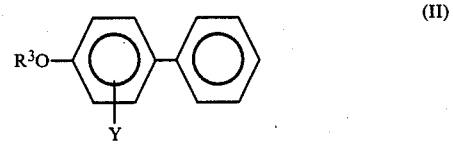

(II)

wherein $R^3$ is a lower alkyl group, and Y is a halogen atom; and

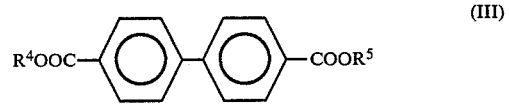

(III)

wherein each of $R^4$ and $R^5$ is a lower alkyl group.

DETAILED DESCRIPTION OF THE INVENTION

Preferable compounds of the general formula (I) are those in which $R^1$ is a substituted or unsubstituted alkenyl group, and X is a hydrogen atom, an alkoxy group, an aralkyloxy group, an aroyloxy group or an alkenyloxy group; those in which $R^1$ is a substituted or unsubstituted cycloalkyl group, and X is a hydrogen atom or $R^2O-$ in which $R^2$ is a substituted or unsubstituted cycloalkyl group; those in which X is a hydrogen atom or $R^2O-$ in which $R^2$ is a substituted or unsubstituted cycloalkylcarbonyl group, and $R^1$ is a substituted or unsubstituted cycloalkylcarbonyl group; those in which $R^1$ is a substituted or unsubstituted alkynyl group, and X is a hydrogen atom or $R^2O-$ in which $R^2$ is a substituted or unsubstituted alkynyl group; and those in which R[1] is a substituted or unsubstituted alkenylcarbonyl group, and X is a hydrogen atom or R[2]O— in which R[2] is a substituted or unsubstituted alkenylcarbonyl group. Those in which X is hydrogen atom is more preferred.

Concrete examples of the compounds of the above general formula (I) include the following compounds:

Compound (I-1)
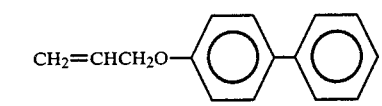

Compound (I-2)
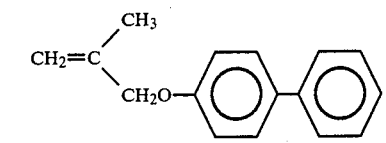

Compound (I-3)
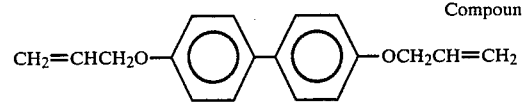

Compound (I-4)
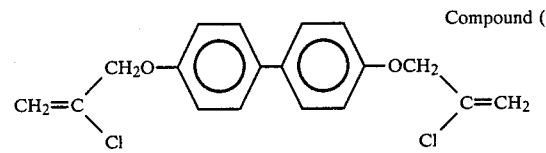

Compound (I-5)
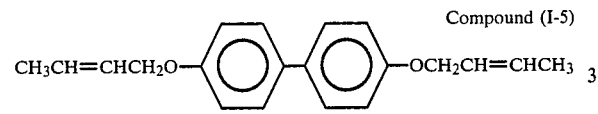

Compound (I-6)
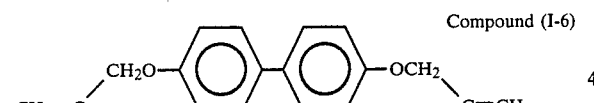

Compound (I-7)
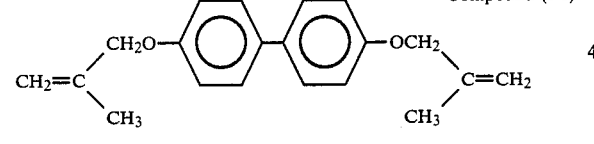

Compound (I-8)
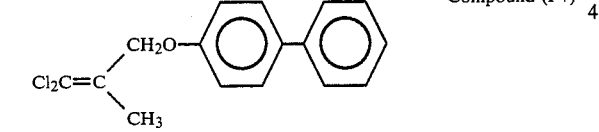

Compound (I-9)
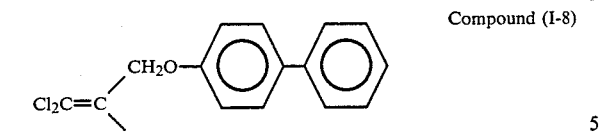

Compound (I-10)
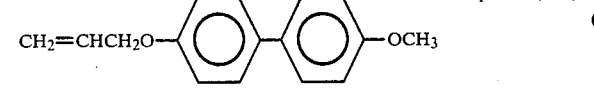

-continued

Compound (I-11)

Compound (I-12)

Compound (I-13)

Compound (I-14)

Compound (I-15)

Compound (I-16)
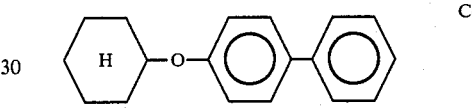

Compound (I-17)
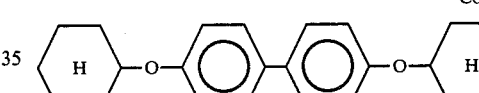

Compound (I-18)
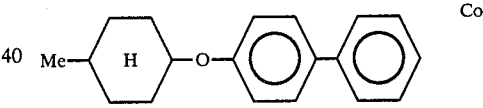

Compound (I-19)
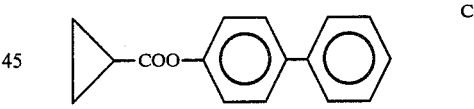

Compound (I-20)
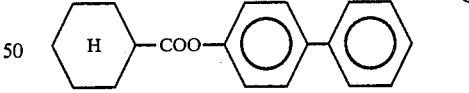

Compound (I-21)
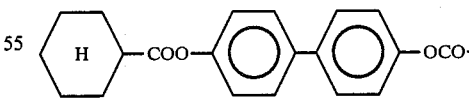

Compound (I-22)
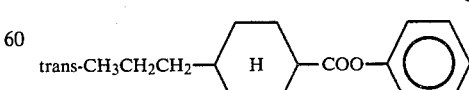

Compound (I-23)
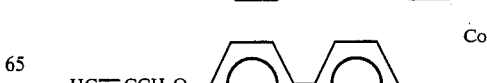

-continued

Compound (I-24)

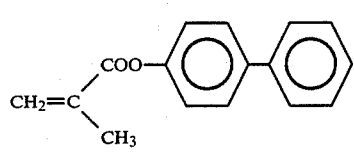
Compound (I-25)

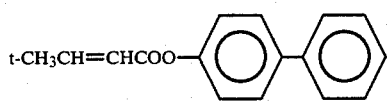
Compound (I-26)

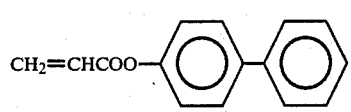
Compound (I-27)

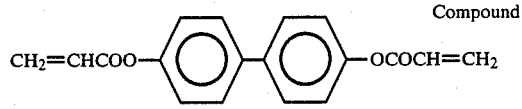
Compound (I-28)

Concrete examples of the compounds of the above general formula (II) are as follows:

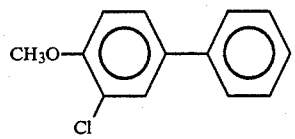
Compound (II-1)

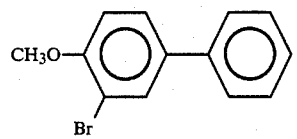
Compound (II-2)

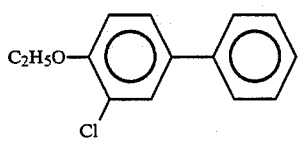
Compound (II-3)

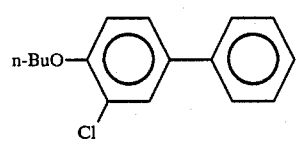
Compound (II-4)

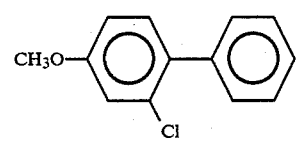
Compound (II-5)

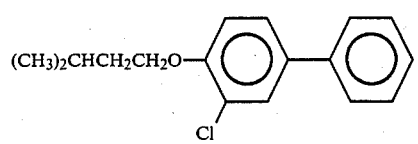
Compound (II-6)

Concrete examples of the compounds of the general formula (III) are as follows:

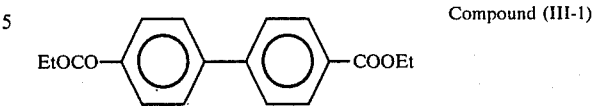
Compound (III-1)

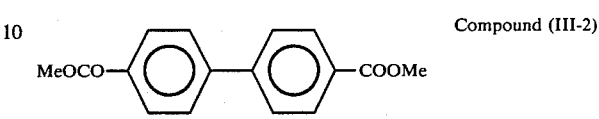
Compound (III-2)

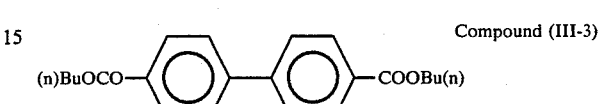
Compound (III-3)

The compounds of the above general formulas can easily be obtained by well-known processes.

The sensitizer according to this invention is added usually in an amount of 5% by weight or more based on the weight of the developer. The adding amount is preferably 10 to 400% by weight, particularly preferably 20 to 300% by weight. When it is less than 5% by weight, no sufficient sensitivity-improving effect can be obtained. On the other hand, an adding amount of more than 400% by weight is economically disadvantageous in some cases.

The main constituents used in the thermal recording material of this invention are concretely explained below, but are not limited to the examples thereof shown below.

The dye precursors include compounds of triphenylmethane series, fluoran series, diphenylmethane series, thiazine series, spiropyran series and the like, for example, 3,3-bis(p-dimethylaminophenyl)-6-dimethylaminophthalide, 3-(4-diethylamino-2-ethoxyphenyl)-3-(1-ethyl-2-methylindole-3-yl)-4-azaphthalide, 3-diethylamino-6-methyl-7-chlorofluoran, 3-diethylamino-7-chlorofluoran, 3-(N-cyclohexylamino)-7-methylfluoran, 3-diethylamino-7-methylfluoran, 3-diethylamino-6-chloro-7-methylfluoran, 3-diethylamino-7-anilinofluoran, 3-diethylamino-6-methyl-7-dibenzylaminofluoran, 3-(N-ethyl-N-p-toluidino)-7-anilinofluoran, 3-diethylamino-7-(o-chloroanilino)fluoran, 3-dibutyl-amino-7-(o-chloroanilino)fluoran, 3-diethylamino-6-methyl-7-anilinofluoran, 3-(N-ethyl-N-p-toluidino)-6-methyl-7-anilinofluoran, 3-(N-methyl-N-cyclohexylamino)-6-methyl-7-anilinofluoran, 3-piperidino-6-methyl-7-anilinofluoran, 3-pyrrolidino-6-methyl-7-anilinofluoran, 3-diethylamino-7-(m-trifluoromethylanilino)fluoran, 3-(N-ethyl-N-isopentylamino)-6-methyl-7-anilinofluoran, 3-diethylamino-6-methyl-7-(p-phenetidino)fluoran, 3-dibutylamino-7-(o-fluoroanilino)fluoran, etc.

As the developer, there are used acidic substances generally used in heat-sensitive paper, namely, electron-accepting compounds. Particularly preferable developers are bisphenols in which one of the hydroxyl groups may optionally be substituted and which are represented by the general formula:

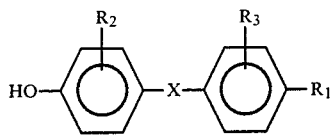

wherein X is

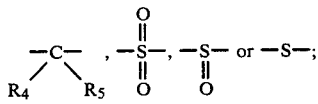

$R_1$ is a hydroxyl group, a lower alkoxy group, a lower alkyl group or a halogen atom; each of $R_2$ and $R_3$ is a hydrogen atom, a lower alkyl group, a lower alkenyl group or a halogen atom; each of $R_4$ and $R_5$ is a hydrogen atom, a lower alkyl group or an alkoxycarbonyl group; and $R_4$ and $R_5$ may be bonded to each other to form a ring.

Concrete examples of the bisphenols in which one of the hydroxyl groups may optionally be substituted include 2,2-bis(4-hydroxyphenyl)propane, 2,2-bis(4-hydroxyphenyl)butane, 2,2-bis(4-hydroxyphenyl)pentane, 2,2-bis(4-hydroxyphenyl)hexane, 1,1-bis(4-hidroxyphenyl)cyclohexane, bis(4-hydroxyphenyl)methane, methyl 2,2-bis(4-hydroxyphenyl)acetate, ethyl 2,2-bis(4-hydroxyphenyl)acetate, n-butyl 2,2-bis(4-hydroxyphenyl)acetate, 2,2-bis(3-chloro-4-hydroxyphenyl)propane, 2,2-bis(3-t-butyl-4-hydroxyphenyl)propane, bis(3-t-butyl-4-hydroxy-5-methylphenyl)sulfide, bis(4-hydroxyphenyl)sulfone, bis(3-allyl-4-hydroxyphenyl)sulfone, bis(4-hydroxyphenyl)sulfoxide, bis(4-hydroxyphenyl)sulfide, 4-hydroxy-4'-isopropyloxydiphenylsulfone, 4-hydroxy-4'-methyldiphenylsulfone, 4-hydroxy-4'-chlorodiphenylsulfone, etc.

Developers other than the bisphenols in which one of the hydroxyl groups may optionally substituted include phenols, aromatic carboxylic acids, N,N'-diarylthioureas, zinc salts or complexes thereof with organic substances, etc. Concrete examples of these compounds are given below. The phenols include phenol, p-t-butylphenol, p-phenylphenol, 1-naphthol, 2-naphthol, p-hydroxyacetophenone, 2,2'-dihydroxybiphenyl, 2,2'-methylenebis(4-chlorophenol), 2,2'-thiobisphenol, 2,2'-thiobis(4,6-dichlorophenol), 2,2'-octylidene-bis(4-methylphenol), 1,7-bis(4-hydroxyphenylthio)-3,5-dioxaheptane, novolak-type phenol resins, p-hydroxybenzoic acid, methyl p-hydroxybenzoate, benzyl p-hydroxybenzoate, lauryl gallate, stearyl gallate, salicylanilide, 5-chlorosalicylanilide, etc. The aromatic carboxylic acids include benzoic acid, p-t-butylbenzoic acid and N,N'-diarylthioureas include N,N'-bis(3-chlorophenyl)thiourea, N,N'-bis(3-trifluorophenyl)thiourea, etc. The zinc salts or complexes thereof with organic substances include zinc 5-t-butylsalycylate, zinc hydroxynaphthoate, zinc thiocyanate, complexes of the zinc thiocyanates of the formula:

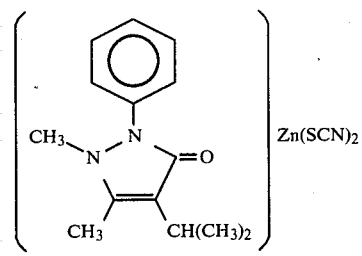

with organic substances, etc.

As binders, there may be used, for example, water-soluble binders such as starches, hydroxyethyl cellulose, methyl cellulose, carboxymethyl cellulose, gelatin, casein, polyvinyl alcohols, modified polyvinyl alcohols, styrene-maleic anhydride copolymers, ethylene-maleic anhydride copolymers, and the like, and latex-type water-soluble binders such as styrene-butadiene copolymers, acrylonitrile-butadiene copolymers, methyl acrylate-butadiene copolymers, and the like.

As pigments, there may be used diatomaceous earth, talc, kaolin, calcined kaolin, calcium carbonate, magnesium carbonate, titanium oxide, zinc oxide, silicon oxide, aluminum hydroxide, urea-formaldehyde resins, etc.

In addition, in order to prevent wear of head, sticking and the like, there may be used metal salts of higher fatty acids such as zinc stearate, calcium stearate and the like, and waxes such as paraffin, oxidized paraffin, polyethylenes, polyethylene oxides, stearic acid amide, castor wax and the like. There may also be used dispersing agents such as sodium dioctylsulfosuccinate and the like; ultraviolet ray absorbing agents of benzophenone type, benzotriazole type and the like; surface active agents; fluorescent dyes; etc.

As a support used in the thermal recording material according to this invention, paper is mainly used, though there may optionally be used various nonwoven fabrics, plastic films, synthetic papers, metalic foils, and composite sheets obtained by combination thereof.

This invention is further explained in more detail with reference to the following synthesis examples and examples, which are not by way of limitation but by way of illustration.

SYNTHESIS EXAMPLE 1

Synthesis of Compound (I-1)

To 100 ml of acetone was added 10.2 g of p-phenylphenol, followed by adding thereto 15.6 g of a 25.6% aqueous sodium hydroxide solution and 9.6 g of allyl bromide. This system was refluxed with stirring for 6 hours, and after the system was allowed to cool, benzene and water were added to carry out separation into two layers. The organic layer was washed with an aqueous sodium hydrogencarbonate solution and dried over anhydrous potassium carbonate. The solvent and the unreacted materials were removed by distillation under reduced pressure, and the residue was treated with n-hexane to obtain crystals of the desired compound.

The crystals were recrystallized from n-hexane to obtain 4.4 g of the desired compound, m.p. 84.5°–85° C., mass spectrum (FD method) m/e 210 (M+).

SYNTHESIS EXAMPLE 2

Synthesis of Compound (I-2)

In the same manner as in Synthesis Example 1, except that 7.5 g of 3-chloro-2-methyl-1-propene was used in place of 9.6 g of allyl bromide and that the heating time was changed to 9 hours, there was obtained 5.8 g of the desired compound, m.p. 75.5°–76° C.

SYNTHESIS EXAMPLE 3

Synthesis of Compound (I-15)

To 60 ml of acetone was added 10.2 g of p-phenylphenol, followed by adding thereto 11.2 g of a 35.7% aqueous sodium hydroxide solution and 11.0 g of cyclopentyl bromide. This system was refluxed with stirring for 10 hours. After the system was allowed to cool, benzene and water were added to carry out separation into two layers, and the organic layer was washed with an aqueous sodium hydrogencarbonate solution and dried over anhydrous potassium carbonate. The solvent was removed by distillation, and the residue was treated with n-hexane to obtain the desired compound, which was then recrystallized from n-hexane to obtain 3.3 g of the desired compound, m.p. 88°–89.5° C.

SYNTHESIS EXAMPLE 4

Synthesis of Compound (I-19)

To 200 ml of acetone was added 34.0 g of p-phenylphenol, followed by adding thereto a 29.9% aqueous sodium hydroxide solution. To this system was added dropwise 25.5 g of cyclopropanecarbonyl chloride with stirring. After the stirring was continued, benzene and water were added to carry out separation into two layers. The organic layer was washed with an aqueous sodium hydrogencarbonate solution and dried over anhydrous potassium carbonate, and the solvent was removed by distillation. The residue was treated with n-hexane and benzene to obtain the desired compound, which was then recrystallized from n-hexane and then from ethanol to obtain 18.3 g of the desired compound, m.p. 107°–110° C.

SYNTHESIS EXAMPLE 5

Synthesis of Compound (I-20)

In the same manner as in Synthesis Example 4, except that 33.5 g of cyclohexanecarboxyl chloride was used in place of 25.5 g of cyclopropanecarbonyl chloride, there was obtained 41.2 g of the desired compound, m.p. 93.5°–94.5° C.

SYNTHESIS EXAMPLE 6

Synthesis of Compound (I-23)

To 100 ml of acetone was added 10.2 g of p-phenylphenol, followed by adding thereto 12.9 g of a 34.1% aqueous sodium hydroxide solution and 9.6 g of propargyl bromide. This system was refluxed with stirring for 5 hours. After the system was allowed to cool, benzene and water were added to carry out separation into two layers. The organic layer was washed with an aqueous sodium hydrogencarbonate solution and dried over anhydrous potassium carbonate. The solvent and the unreacted materials were removed by distillation under reduced pressure, and the residue was treated with n-hexane to obtain crystals of the desired compound. The crystals were recrystallized from n-hexane to obtain 8.6 g of the desired compound, m.p. 80.5°–83° C., mass spectrum (FD method) m/e 208.

SYNTHESIS EXAMPLE 7

Synthesis of Compound (I-25)

To 60 ml of acetone was added 10.2 g of p-phenylphenol, followed by adding thereto 12.5 g of a 28.8% aqueous sodium hydroxide solution. Thereto was added dropwise 7.6 g of methacrylic acid chloride with stirring over a period of 10 minutes. This system was stirred for 13 minutes, after which benzene and water were added to carry out separation into two layers. The organic layers was washed with an aqueous sodium hydrogencarbonate solution and dried over anhydrous potassium carbonate. The solvent was removed by distillation and the residue was treated with n-hexane to obtain crystals of the desired compound. The crystals were recrystallized from n-hexane and then from ethanol to obtain 5.9 g of the desired compound, m.p. 108°–109.5° C. mass spectrum (FD method) m/e 238.

SYNTHESIS EXAMPLE 8

Synthesis of Compound (I-26)

In the same manner as in Synthesis Example 7, except that crotonyl chloride was used in place of methacrylic acid chloride, there was obtained 10.6 g of the desired compound, m.p. 80°–82° C., mass spectrum (FD method) m/e 238.

SYNTHESIS EXAMPLE 9

Synthesis of Compound (I-27)

In the same manner as in Synthesis Example 7, except that 6.5 g of acrylic acid chloride was used in place of 7.6 g of methacrylic acid chloride, there was obtained 5.7 g of the desired compound, m.p. 59°–61° C., mass spectrum (FD method) m/e 224.

SYNTHESIS EXAMPLE 10

Synthesis of Compound (II-1)

To 60 ml of acetone was added 12.3 g of 2-chloro-4-phenylphenol, followed by adding thereto a 33.9% aqueous sodium hydroxide solution. Thereto was added dropwise 9.8 g of dimethylsulfuric acid with stirring over a period of 2 minutes, and the resulting mixture was stirred for 2 hours and 30 minutes, after which benzene and water were added to carry out separation into two layers. The organic layer was washed with an aqueous sodium hydrogencarbonate solution and dried over anhydrous potassium carbonate. The solvent was removed by distillation and the residue was treated with n-hexane to obtain the desired compound, which was then recrystallized from n-hexane to obtain 6.6 g of the desired compound, m.p. 93°–95° C.

EXAMPLE 1

By means of a ball mill, 20 g of 3-diethylamino-6-methyl-7-anilinofluoran and 80 g of a 1% aqueous polyvinyl alcohol solution were made into a dispersion. On the other hand, 50 g of 2,2-bis(hydroxyphenyl)propane and 200 g of a 1% aqueous polyvinyl alcohol solution were made into a dispersion by means of a ball mill, and 50 g of Compound (I-1) and 200 g of a 1% aqueous polyvinyl alcohol solution were similarly made into a dispersion.

These three dispersions were mixed, after which 125 g of a 40% dispersion of calcium carbonate was added, followed by adding thereto 40 g of a 25% dispersion of zinc stearate and 285 g of a 10.5% aqueous polyvinyl alcohol solution, and the resulting mixture was sufficiently stirred to prepare a coating fluid. The coating fluid was coated on base paper having a basis weight of 55 g/m² in an amount of 6 g/m² in terms of solids, and dried, and the base paper was then treated by means of a super calendar to obtain a thermal recording material.

COMPARATIVE EXAMPLE 1

A thermal recording material was obtained in the same manner as in Example 1, except that N-(hydroxymethyl)stearic acid amide was used in place of Compound (I-1).

COMPARATIVE EXAMPLE 2

A thermal recording material was obtained in the same manner as in Example 1, except that 2-benzyloxynaphthalene was used in place of Compound (I-1).

COMPARATIVE EXAMPLE 3

A thermal recording material was obtained in the same manner as in Example 1, except that the dispersion of Compound (I-1) was omitted.

EVALUATION

The thermal recording materials obtained in Example 1 and Comparative Examples 1 to 3 were subjected to recording by means of a facsimile tester under the conditions of an applied voltage of 15.5 V and a pulse duration of 1.0 milliseconds, 1.5 milliseconds or 2.0 milliseconds, and the optical density of the colored images thus formed was measured by means of Macbeth RD-918. The results obtained are tabulated below.

|  | Pulse duration (millisecond) | | |
| --- | --- | --- | --- |
|  | 1.0 | 1.5 | 2.0 |
| Example 1 | 0.68 | 1.10 | 1.25 |
| Comparative Example 1 | 0.32 | 0.79 | 1.19 |
| Comparative Example 2 | 0.38 | 0.86 | 1.11 |
| Comparative Example 3 | 0.12 | 0.35 | 0.72 |

EXAMPLE 2

By means of a ball mill, 20 g of 3-diethylamino-6-methyl-7-anilinofluoran and 80 g of a 1% aqueous polyvinyl alcohol were made into a dispersion. On the other hand, 50 g of 2,2-bis(4-hydroxyphenyl)propane and 200 g of a 1% aqueous polyvinyl alcohol solution were made into a dispersion by means of a ball mill, and 50 g of Compound (I-15) and 200 g of a 1% aqueous polyvinyl alcohol solution were similarly made into a dispersion.

These three dispersions were mixed, after which 125 g of a 40% dispersion of calcium carbonate was added, followed by adding thereto 40 g of a 25% dispersion of zinc stearate and 285 g of a 10.5% aqueous polyvinyl alcohol solution, and the resulting mixture was sufficiently stirred to prepare a coating fluid. The coating fluid was coated on base paper having a basis weight of 55 g/m² in an amount of 6 g/m² in terms of solids, and dried, and the base paper was then treated by means of a super calendar to obtain a thermal recording material.

COMPARATIVE EXAMPLE 4

A thermal recording material was obtained in the same manner as in Example 2, except that N-(hydroxymethyl)stearic acid amide was used in place of Compound (I-15).

COMPARATIVE EXAMPLE 5

A thermal recording material was obtained in the same manner as in Example 2, except that the dispersion of Compound (I-15) was omitted.

EVALUATION

The thermal recording materials obtained in Example 2 and Comparative Examples 4 and 5 were subjected to recording by means of FACOM FAX-621C, a facsimile machine manufactured by Fujitsu, Ltd. and the optical density of the images thus formed was measured by using Macbeth RD-514. The results obtained are tabulated below.

TABLE

|  | Optical density |
| --- | --- |
| Example 2 | 1.08 |
| Comparative Example 4 | 0.68 |
| Comparative Example 5 | 0.23 |

EXAMPLE 3

By means of a ball mill, 20 g of 3-diethylamino-6-methyl-7-anilinofluoran and 80 g of a 1% aqueous polyvinyl alcohol solution were made into a dispersion. On the other hand, 50 g of 2,2-bis(4-hydroxyphenyl)propane and 200 g of a 1% aqueous polyvinyl alcohol solution were made into a dispersion by means of a ball mill, and 50 g of Compound (I-19) and 200 g of a 1% aqueous polyvinyl alcohol solution were similarly made into a dispersion.

These three dispersions were mixed, after which 125 g of a 40% dispersion of calcium carbonate was added, followed by adding thereto 40 g of a 25% dispersion of zinc stearate and 285 g of a 10.5% aqueous polyvinyl alcohol solution, and the resulting mixture was sufficiently stirred to prepare a coating fluid. The coating fluid was coated on base paper having a basis weight of 55 g/m² in an amount of 6 g/m² in terms of solids, and dried, and the base paper was then treated by means of a super calendar to obtain a thermal recording material.

EXAMPLE 4

A thermal recording material was obtained in the same manner as in Example 3, except that Compound (I-20) was used in place of Compound (I-19).

COMPARATIVE EXAMPLE 6

A thermal recording material was obtained in the same manner as in Example 3, except that the dispersion of Compound (I-19) was omitted.

EVALUATION

Evaluation was carried out on the thermal recording materials obtained in Examples 3 and 4 and Comparative Example 6 in the same manner as carried out for the materials obtained in Example 2 and Comparative Examples 4 and 5 and the results are shown in the following table.

TABLE

| | Optical density |
|---|---|
| Example 3 | 0.79 |
| Example 4 | 0.70 |
| Comparative Example 6 | 0.23 |

EXAMPLE 5

By means of a ball mill, 20 g of 3-diethylamino-6-methyl-7-anilinofluoran and 80 g of a 1% aqueous polyvinyl alcohol solution were made into a dispersion. On the other hand, 50 g of 2,2-bis(4-hydroxyphenyl)propane and 200 g of a 1% aqueous polyvinyl alcohol solution were made into a dispersion by means of a ball mill, and 50 g of Compound (I-23) and 200 g of a 1% aqueous polyvinyl alcohol solution were similarly made into a dispersion.

These three dispersions were mixed, after which 125 g of a 40% dispersion of calcium carbonate was added, followed by adding thereto 40 g of a 25% dispersion of zinc stearate and 285 g of a 10.5% aqueous polyvinyl alcohol solution, and the resulting mixture was sufficiently stirred to prepare a coating fluid. The coating fluid was coated on base paper having a basis weight of 55 g/m$^2$ in an amount of 6 g/m$^2$ in terms of solids, and dried, and the base paper was then treated by means of a super calender to obtain a thermal recording material.

COMPARATIVE EXAMPLE 7

A thermal recording material was obtained in the same manner as in Example 5, except that N-(hydroxymethyl)stearic acid amide was used in place of Compound (I-23).

COMPARATIVE EXAMPLE 8

A thermal recording material was obtained in the same manner as in Example 5, except that the dispersion of Compound (I-23) was omitted.

EVALUATION

Evaluation was carried out on the thermal recording materials obtained in Example 5 and Comparative Examples 7 and 8 in the same manner as carried out for the materials obtained in Example 2 and Comparative Examples 4 and 5 and the results obtained are tabulated below.

TABLE

| | Optical density |
|---|---|
| Example 5 | 1.12 |
| Comparative Example 7 | 0.68 |
| Comparative Example 8 | 0.23 |

EXAMPLE 6

By means of a ball mill, 20 g of 3-diethylamino-6-methyl-7-anilinofluoran and 80 g of a 1% aqueous polyvinyl alcohol solution were made into a dispersion. On the other hand, 50 g of 2,2-bis(4-hydroxyphenyl)propane and 200 g of a 1% aqueous polyvinyl alcohol solution were made into a dispersion by means of a ball mill, and 50 g of Compound (I-25) and 200 g of a 1% aqueous polyvinyl alcohol solution were similarly made into a dispersion.

These three dispersions were mixed, after which 125 g of a 40% dispersion of calcium carbonate was added, followed by adding thereto 40 g of a 25% dispersion of zinc stearate and 285 g of a 10.5% aqueous polyvinyl alcohol solution, and the resulting mixture was sufficiently stirred to prepare a coating fluid. The coating fluid was coated on base paper having a basis weight of 55 g/m$^2$ in an amount of 6 g/m$^2$ in terms of solids, and dried, and the base paper was then treated by means of a super calender to obtain a thermal recording material.

EXAMPLE 7

A thermal recording material was obtained in the same manner as in Example 6, except that Compound (I-26) was used in place of Compound (I-25).

EXAMPLE 8

A thermal recording material was obtained in the same manner as in Example 6, except that Compound (I-27) was used in place of Compound (I-25).

COMPARATIVE EXAMPLE 9

A thermal recording material was obtained in the same manner as in Example 6, except that N-(hydroxymethyl)stearic acid amide was used in place of Compound (I-25).

COMPARATIVE EXAMPLE 10

A thermal recording material was obtained in the same manner as in Example 6, except that the dispersion of Compound (I-25) was omitted.

Evaluation was carried out on the thermal recording materials obtained in Examples 6 to 8 and Comparative Examples 9 and 10 in the same manner as carried out for the materials obtained in Example 2 and Comparative Examples 4 and 5. The results obtained are tabulated below.

TABLE

| | Optical density |
|---|---|
| Example 6 | 1.06 |
| Example 7 | 0.85 |
| Example 8 | 1.08 |
| Comparative Example 9 | 0.68 |
| Comparative Example 10 | 0.23 |

EXAMPLE 9

By means of a ball mill, 20 g of 3-diethylamino-6-methyl-7-anilinofluoran and 80 g of a 1% aqueous polyvinyl alcohol solution were made into a dispersion. On the other hand, 50 g of 2,2-bis(4-hydroxyphenyl)propane and 200 g of a 1% aqueous polyvinyl alcohol solution were made into a dispersion by means of a ball mill, and 50 g of Compound (II-1) and 200 g of a 1% aqueous polyvinyl alcohol solution were similarly made into a dispersion.

These three dispersions were mixed, after which 125 g of a 40% dispersion of calcium carbonate was added, followed by adding 40 g of a 25% dispersion of zinc stearate and 285 g of a 10.5% aqueous polyvinyl alcohol solution, and the resulting mixture was sufficiently stirred to prepare a coating fluid. The coating fluid was coated on base paper having a basis weight of 55 g/m$^2$ in an amount of 6 g/m$^2$ in terms of solids, and dried, and the base paper was then treated by means of a super calender to obtain a thermal recording material.

COMPARATIVE EXAMPLE 11

A thermal recording material was obtained in the same manner as in Example 9, except that N-(hydroxymethyl)stearic acid amide was used in place of Compound (II-1).

COMPARATIVE EXAMPLE 12

A thermal recording material was obtained in the same manner as in Example 9, except that the dispersion of Compound (II-1) was omitted.

Evaluation was carried out on the thermal recording materials obtained in Example 9 and Comparative Examples 11 and 12 in the same manner as carried out for the materials obtained in Example 2 and Comparative Examples 4 and 5. The results obtained are tabulated below.

TABLE

|  | Optical density |
|---|---|
| Example 9 | 1.06 |
| Comparative Example 11 | 0.68 |
| Comparative Example 12 | 0.23 |

EXAMPLE 10

By means of a ball mill, 20 g of 3-diethylamino-6-methyl-7-anilinofluoran and 80 g of a 1% aqueous polyvinyl alcohol solution were made into a dispersion. On the other hand, 50 g of 2,2-bis(4-hydroxyphenyl)propane and 200 g of a 1% aqueous polyvinyl alcohol solution were made into a dispersion by means of a ball mill, and 50 g of Compound (III-1) and 200 g of a 1% aqueous polyvinyl alcohol solution were similarly made into a dispersion.

These three dispersions were mixed, after which 125 g of a 40% dispersion of calcium carbonate was added, followed by adding thereto 40 g of a 25% dispersion of zinc stearate and 285 g of a 10.5% aqueous polyvinyl alcohol solution, and the resulting mixture was sufficiently stirred to prepare a coating fluid. The coating fluid was coated on base paper having a basis weight of 55 g/m² in an amount of 6 g/m² in terms of solids, and dried, and the base paper was then treated by means of a super calender to obtain a thermal recording material.

COMPARATIVE EXAMPLE 13

A thermal recording material was obtained in the same manner as in Example 10, except that the dispersion of Compound (III-1) was omitted.

Evaluation was carried out by the thermal recording materials obtained in Example 10 and Comparative Example 13 in the same manner as carried out for the materials obtained in Example 2 and Comparative Examples 4 and 5. The results obtained are tabulated below.

TABLE

|  | Optical density |
|---|---|
| Example 10 | 0.74 |
| Comparative Example 13 | 0.23 |

What is claimed is:

1. A thermal recording material comprising a usually colorless or light-colored dye precursor and a developer which reacts therewith to cause color development thereof on heating, which contains at least one compound selected from the group consisting of Compounds represented by the general formulas (I), (II) and (III):

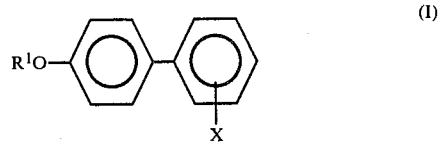

(I)

wherein $R^1$ is a substituted or unsubstituted alkenyl group, a substituted or unsubstituted cycloalkyl group, a substituted or unsubstituted cycloalkylcarbonyl group, a substituted or unsubstituted alkynyl group, or a substituted or unsubstituted alkenylcarbonyl group, and X is a hydrogen atom, an alkoxy group, an aralkyloxy group, an aroyloxy group, an alkenyloxy group, or $R^2O-$ in which $R^2$ is a substituted or unsubstituted cycloalkyl group, a substituted or unsubstituted cycloalkylcarbonyl group, a substituted or unsubstituted alkynyl group, or a substituted or unsubstituted alkenylcarbonyl group;

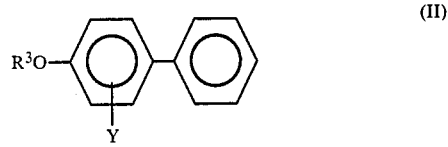

(II)

wherein $R^3$ is a lower alkyl group, and Y is a halogen atom; and

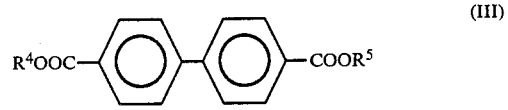

(III)

wherein each of $R^4$ and $R^5$ is a lower alkyl group.

2. A thermal recording material according to claim 1, wherein in the general formula (I), $R^1$ is a substituted or unsubstituted alkenyl group, and X is a hydrogen atom, an alkoxy group, an aralkyloxy group, an aroyloxy group or an alkenyloxy group.

3. A thermal recording material according to claim 2, wherein the compound of the general formula (I) is

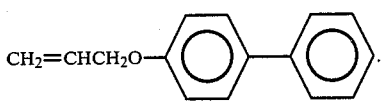

4. A thermal recording material according to claim 2, wherein X in the general formula (I)f is a hydrogen atom.

5. A thermal recording material according to claim 1, wherein in the general formula (I), $R^1$ is a substituted or unsubstituted cycloalkyl group, and X is a hydrogen atom or $R^2O-$ in which $R^2$ is a substituted or unsubstituted cycloalkyl group.

6. A thermal recording material according to claim 5, wherein the compound of the general formula (I) is

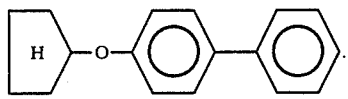

7. A thermal recording material according to claim 5, wherein X in the general formula (I) is a hydrogen atom.

8. A thermal recording material according to claim 7, wherein the developer is 2,2-bis(4-hydroxyphenyl)propane.

9. A thermal recording material according to claim 1, wherein in the general formula (I), X is a hydrogen atom or $R^2O-$ in which $R^2$ is a substituted or unsubstituted cycloalkylcarbonyl group, and $R^1$ is a substituted or unsubstituted cycloalkylcarbonyl group.

10. A thermal recording material according to claim 9, wherein the compound of the general formula (I) is

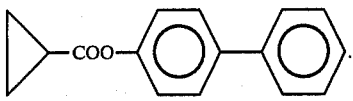

11. A thermal recording material according to claim 9, wherein the compound of the general formula (I) is

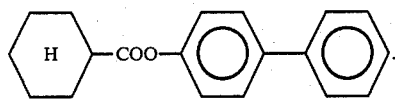

12. A thermal recording material according to claim 9, wherein X in the general formula (I) is a hydrogen atom.

13. A thermal recording material according to claim 1, wherein in the general formula (I), $R^1$ is a substituted or unsubstituted alkynyl group, and X is a hydrogen atom or $R^2O-$ in which $R^2$ is a substituted or unsubstituted alkynyl group.

14. A thermal recording material according to claim 13, wherein the compound of the general formula (I) is

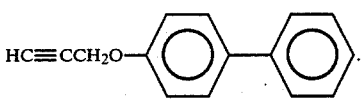

15. A thermal recording material according to claim 13, wherein X in the general formula (I) is a hydrogen atom.

16. A thermal recording material according to claim 1, wherein in the general formula (I), $R^1$ is a substituted or unsubstituted alkenylcarbonyl group, and X is a hydrogen atom or $R^2O-$ in which $R^2$ is a substituted or unsubstituted alkenylcarbonyl group.

17. A thermal recording material according to claim 16, wherein the compound of the general formula (I) is

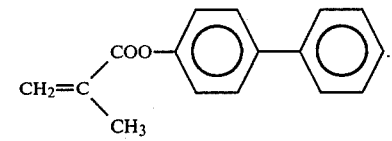

18. A thermal recording material according to claim 16, wherein the compound of the general formula (I) is

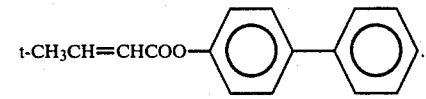

19. A thermal recording material according to claim 16, wherein the compound of the general formula (I) is

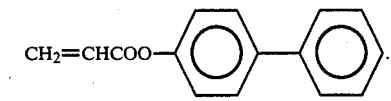

20. A thermal recording material according to claim 16, wherein X in the general formula (I) is a hydrogen atom.

21. A thermal recording material according to claim 1, wherein the compound of the general formula (II) is

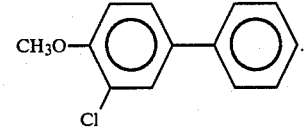

22. A thermal recording material according to claim 1, wherein the compound of the general formula (III) is

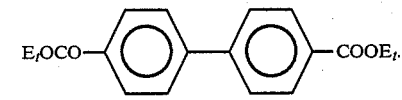

23. A thermal recording material according to claim 1, wherein X in the general formula (I) is a hydrogen atom.

24. A thermal recording material according to claim 1, wherein the amount of the compound is 5% by weight or more based on the weight of the developer.

25. A thermal recording material according to claim 24, wherein the amount of the compound is 20 to 300% by by weight based on the weight of the developer.

26. A thermal recording material according to claim 1, wherein the developer is a bisphenol series compound in which one of the hydroxyl groups may optionally be substituted.

* * * * *